US009839258B2

(12) United States Patent
Zahrieh (10) Patent No.: US 9,839,258 B2
(45) Date of Patent: Dec. 12, 2017

(54) VIBRATING FOOT MASSAGER

(71) Applicant: Sanad Zahrieh, Brooklyn, NY (US)

(72) Inventor: Sanad Zahrieh, Brooklyn, NY (US)

( * ) Notice: Subject to any disclaimer, the term of this patent is extended or adjusted under 35 U.S.C. 154(b) by 378 days.

(21) Appl. No.: 14/737,639

(22) Filed: Jun. 12, 2015

(65) Prior Publication Data

US 2016/0361230 A1    Dec. 15, 2016

(51) Int. Cl.
| | |
|---|---|
| *A61H 39/00* | (2006.01) |
| *A43B 7/14* | (2006.01) |
| *A61H 23/02* | (2006.01) |
| *A61N 1/00* | (2006.01) |
| *G06F 19/00* | (2011.01) |
| *A61H 7/00* | (2006.01) |
| *A61N 1/04* | (2006.01) |
| *A61N 1/36* | (2006.01) |

(52) U.S. Cl.
CPC ............. *A43B 7/146* (2013.01); *A61H 23/02* (2013.01); *A61N 1/00* (2013.01); *G06F 19/3481* (2013.01); *A61H 7/004* (2013.01); *A61H 2201/0107* (2013.01); *A61H 2201/0207* (2013.01); *A61H 2201/0228* (2013.01); *A61H 2201/10* (2013.01); *A61H 2201/164* (2013.01); *A61H 2201/165* (2013.01); *A61H 2201/5002* (2013.01); *A61H 2201/5005* (2013.01); *A61H 2201/5007* (2013.01); *A61H 2201/5097* (2013.01); *A61H 2205/065* (2013.01); *A61H 2205/125* (2013.01); *A61N 1/0452* (2013.01); *A61N 1/0484* (2013.01); *A61N 1/36003* (2013.01)

(58) Field of Classification Search
CPC .............. A61H 23/02; A61H 2205/125; A61H 2201/0107; A61H 2201/0207; A61H 2201/0228; A61H 2201/10; A61H 2201/164; A61H 2201/165; A61H 2201/5002; A61H 2201/5005; A61H 2201/5007; A61H 2201/5097; A61H 2201/125; A61H 1/0484; A61H 1/36003; A61H 1/0452; A43B 7/146; G06F 19/3481

See application file for complete search history.

(56) References Cited

U.S. PATENT DOCUMENTS

| | | | |
|---|---|---|---|
| 5,913,838 A | 6/1999 | Reilly | |
| 6,258,048 B1 * | 7/2001 | Montague | A61H 7/001 601/115 |
| 6,345,454 B1 | 2/2002 | Cotton | |

(Continued)

FOREIGN PATENT DOCUMENTS

| | | |
|---|---|---|
| CN | 2585570 Y | 11/2003 |
| CN | 201146871 Y | 11/2008 |

(Continued)

*Primary Examiner* — Glenn Richman
(74) *Attorney, Agent, or Firm* — Gearhart Law LLC (57) ABSTRACT

The application provides for a vibrating foot massager that resembles a common shoe. This vibrating foot massager has a number of vibrating motors which can be placed in a variety of combinations within the sole of the shoe. Preferably, the vibrating foot massager will be equipped with a power source so the entire device will be portable. This will enable a user to enjoy the benefits of receiving a foot massage while on the go. The vibrating foot massager is also equipped with a power switch such that when the motors are not in use, the device operates as a functional shoe.

19 Claims, 10 Drawing Sheets

(56) References Cited

U.S. PATENT DOCUMENTS

| | | | |
|---|---|---|---|
| 7,603,797 B2 | 10/2009 | Chung | |
| 7,614,168 B1 * | 11/2009 | Zummer | A61H 15/0078 36/141 |
| 7,832,124 B2 * | 11/2010 | Blockton | A43B 3/0005 36/136 |
| 8,209,883 B2 * | 7/2012 | Lyden | A43B 1/0081 2/239 |
| 8,322,055 B1 * | 12/2012 | Saint-Cyr | A61H 23/02 36/141 |

FOREIGN PATENT DOCUMENTS

| | | |
|---|---|---|
| CN | 201160541 Y | 12/2008 |
| CN | 101869531 A | 10/2010 |
| CN | 202364931 U | 8/2012 |
| CN | 203087697 U | 7/2013 |
| EP | 2782542 A1 | 10/2014 |
| WO | 2012069553 A1 | 5/2012 |

* cited by examiner

VIBRATING FOOT MASSAGER

CLAIM OF PRIORITY

This application claims no priority to any patent or patent application.

FIELD OF THE EMBODIMENTS

The invention and its embodiments relate to footwear, in particular a wearable vibrating foot massager.

BACKGROUND OF THE EMBODIMENTS

The foot is one of the most complex portions of the human body and due in part to that fact, foot problems are pervasive throughout today's society. Affecting various parts of the foot's 26 bones, 42 muscles, 33 joints, and more than 50 ligaments and tendons, a wide variety of foot problems exist. The foot has many pressure points, each of which is related to a different part of the body.

This foot-body part relationship is part of the larger reflexology movement. While expert disagree on the finer points of how reflexology works, the general consensus is that certain parts of the foot, when stimulated, can generate relief in other parts of the body. Put simply, reflexology is an art of natural healing based on the principle that there are pressure points (reflexes) in the feet, hands and ears, and each point (zone) corresponds to every part, gland and organ of the body. Through the targeted stimulation of these zones relieves tension, one can improve their circulation and encourage the natural function of various areas of the body.

These directed massage techniques can have a wide variety of benefits. As stated, through the calculated manipulation of these pressure points, one can induce the relief of back pain as well as the relief of headaches. Further, through the proper stimulation of these zones, it has been shown that a person may soothe their eyes, ears, trapezius, long bronchus, shoulders, liver, gall bladder, kidneys, urethral canal, ascending colon, small intestine, knees, vermiform appendix, angiomatosis, paranasal cavity, left cerebrum, right cerebrum, nose, pituitary gland, neck, lymph, parathyroid glands, stomach, renal glands, pancreas, duodenum, transverse colon, bladder, heart, genitalia, and much more. Thus the present invention has wide-applicability in treating various ailments.

However, many people struggle to find the time to engage in these treatments, particularly because they require a user to remain stationary for extended periods of time.

Thus, there is a need for a device that allows for a user to enjoy directed massages while on-the-go. The present invention and its embodiments meet and exceed this objective.

REVIEW OF RELATED TECHNOLOGY

U.S. Pat. No. 5,913,838 teaches a vibrating foot massage insole apparatus comprising an insole means having an upper portion, a lower portion, a heel portion and a toe portion; vibrator means mounted on said lower portion of said insole means; power supply means; battery means mounted in said power supply means; control means mounted in said power supply means; and electrical connection means with said electrical connection means connecting said vibrator means, said battery means, said power supply means and said control means, wherein said electrical connection means comprises electrical cable means and further comprising wire retracting means disposed on said power supply means for retracting said electrical cable means.

U.S. Pat. No. 7,603,797 teaches a portable shoe comprising a shoe body and a toe-separating massager, wherein the shoe body having a shoe sole and a vamp, and a front end of the top surface of the shoe sole is formed with a containing groove for fixing the toe-separating massager. The toe-separating massager is disposed with a plurality of separating posts and engaging grooves on the top surface thereof that are arranged staggered, and each engaging groove is engaged with a rotatable biochemical ball. By such arrangements, when the user puts on the shoe, the present invention can rectify the positions of the toes and can massage the toes by the bioelectricity discharged by the biochemical balls.

U.S. Pat. No. 6,258,048 teaches an electric foot massaging assembly wherein a flexible slipper is positioned on the slipper mount with an opening formed in an upper extent thereof for receiving a foot therein. A roller assembly includes a plurality of rollers mounted on the slipper mount for massaging a foot within the slipper. A motor is included for rotating the rollers.

CN202364931 teaches a foot massage shoes, including an insole and sole massage room set up a drug cushion, cushion drugs made from breathable material coated with herbs, the sole or set the battery pack on the vamp, the battery pack with a vibrator connected by wires, a switch button to connect and control the vibrator switch through the wire and battery components.

CN 203087697 teaches an interchangeable soles slippers, including: slippers (I); wherein: slipper insoles (I) within (2), the insole (2) magnet (3); slippers (I) the lower part of Additional insole (4), the magnet attached within the insole (5).

WO2012/069553 and EP2782542disclose a foot massager comprising a motor and a human foot receiver holding assembly comprising at least one human foot receiver for constraining at least one foot therein wherein the motor is provided for driving the human foot receivers such as to massage feet in the human foot receivers holding assembly, characterized in that the foot massager is provided with an eccentric block such that the motor, the eccentric block, the human foot receiver holding assembly and the human foot receiver are interconnected such that when driven by the motor the human foot receiver describes an elliptical translational movement such that the rotation axis of the elliptical translational movement intersects with the longitudinal direction of said human foot receiver and wherein the elliptical translational movement is a vibrating movement with a frequency between 35 and 50 Hz.

Various devices are known in the art. However, their structure and means of operation are substantially different from the present invention. Such devices fail to provide a device that can be easily operated through medical gloves and that provide a tool that can be used on a wider array of hemorrhoidal tissue. Further, the prior art teaches devices that are difficult to release suction with, provide for a poor fit within a patients rectum, and are so large that significant discomfort is caused in a patient being treated. At least one embodiment of this invention is presented in the drawings below and will be described in more detail herein.

SUMMARY OF THE EMBODIMENTS

The present invention discloses a vibrating foot massager, comprising: a bottom portion; a custom sole, having a top layer and a bottom layer, wherein said top layer is equipped with at least one terminal slot and a plurality of raised bumps, wherein said bottom layer is equipped with a plurality of motors, wherein said custom sole is shaped complimentarily to said bottom portion; an interfacing sole, equipped with a plurality of holes, a plurality of pegs, and at least one terminal wherein said interfacing sole is shaped complimentarily to said bottom portion and said custom sole, wherein said at least one terminal is inserted through said at least one terminal slot and into said bottom layer of said custom sole, and wherein said plurality of pegs are capable of securing said interfacing layer to said bottom portion; a top portion, having a power switch, a connection mechanism, and a strap connected to said connection mechanism, wherein said connection mechanism is connected to said at least one terminal, wherein said strap houses a power supply, wherein said power supply is operatively connected to said plurality of motors via said connection mechanism and said at least one terminal, wherein said power switch controls the flow of power from said power source to said at least one motor.

One benefit of providing for multiple configurations is to utilize the targeted stimulation of various pressure points in the foot. By inserting a custom sole with a proper configuration, a user may use the present invention to cure a number of ailments.

The present invention provides for a wearable, interchangeable, modular, vibrating foot massager.

It is an object of the present invention to provide a device capable of giving a user a foot massage.

It is an object of the present invention to provide a means for giving targeted foot massages.

It is an object of the present invention to provide a wearable foot massaging device.

It is an object of the present invention to provide a modular foot massaging device.

It is an object of the present invention to allow users to stimulate particular pressure points.

It is an object of the present invention to provide a relaxing experience without having to be stationary, or stay in an upright position.

DESCRIPTION OF THE PREFERRED EMBODIMENTS

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

In a preferred embodiment, the present invention consists of a slipper capable of that is equipped with at least one vibrating motor. It should be noted that a wide variety of motors at suitable for this purpose, the appropriateness of said motors being determined be the force of the vibration a user desires as well as the size of a user's foot.

The present invention consists of a slipper that is capable of massaging a user's feet that a user may also be used both indoors and outdoors. One benefit of this device is that many different combinations of vibrating motors exist allowing a user a wide range of customizability in how their foot is massaged. Additionally, these motors are readily substitutable and re-arrangeable, making it easy to reconfigure the device.

The motors of the present invention are substituted or rearranged by first detaching the bottom portion. When removed, the bottom portion exposes the custom sole, having a top and bottom part. By replacing the custom sole and employing the plurality of lock-in pegs to reattach the top portion to the bottom portion, a user has effectively substituted one configuration of motors for an alternative configuration.

In a preferred embodiment, several micro coin cell motors are employed to generate the vibrations. It should be noted that in some embodiments, the top portion and bottom portion of the present invention are removable detachable. In these embodiments, the custom sole may be readily replaced with a custom sole of a similar or different configuration. In other embodiments, the top portion and bottom portion of the present invention are of a solitary construction. In these cases, a user would have to don a different embodiment of the present invention if they desired to stimulate a different area of their feet. It should be noted that while the components of the present invention are depicted as being of a particular shape, many shapes are suitable provided that the bottom portion, the custom sole, the interfacing sole, and the top portion are all shaped complimentarily to each other.

Figure 1:
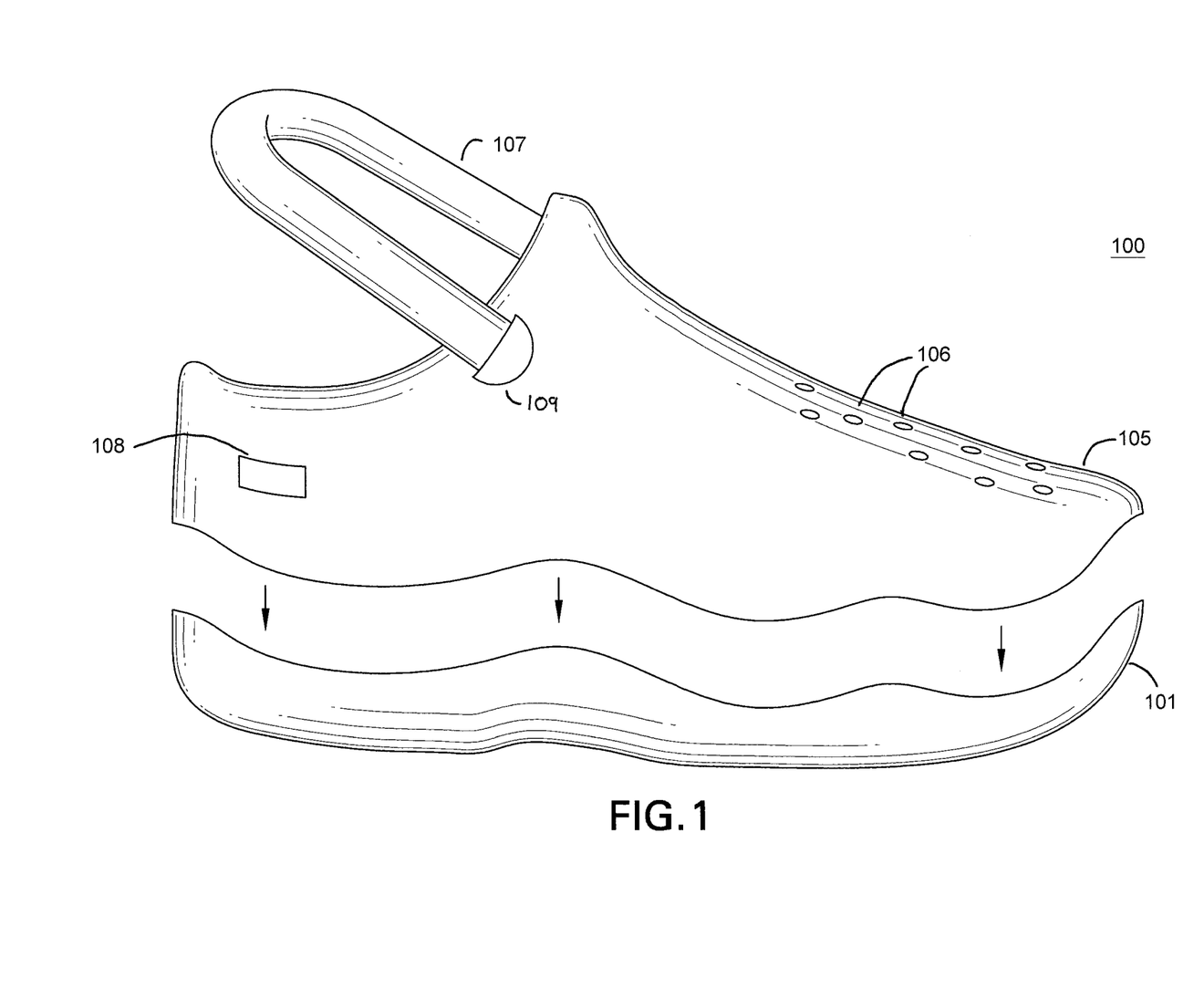
FIG. 1 is a side view of an embodiment of the present invention showing its separable nature.

Referring to FIG. 1, a side view of an embodiment of the present invention showing its separable nature is provided for. In this figure, vibrating foot massager 100 is shown. Further, bottom portion 101, top portion 105, plurality of holes 106, strap 107, power switch 108, and connection mechanism 109 are also shown. This figure shows an embodiment of the present invention where the top portion 105 is removably detachable from bottom portion 101. This allows a user to easily switch out, as a single unit, top portion and bottom portion of custom sole 102 and 103 (See FIG. 8). In some embodiments, the present invention is not equipped with plurality of holes 106. While plurality of holes 106 provides additional ventilation, they are not necessary for the present invention to function. Power switch 108 allows a user to conveniently operate the present invention. This is of particular importance because many users of the present invention will likely be suffering from back pain and other ailments that limit their mobility. In a preferred embodiment, the present invention is equipped with a power source, contained within strap 107. Preferably, this power source will be a rechargeable electrochemical cell.

Figure 2:
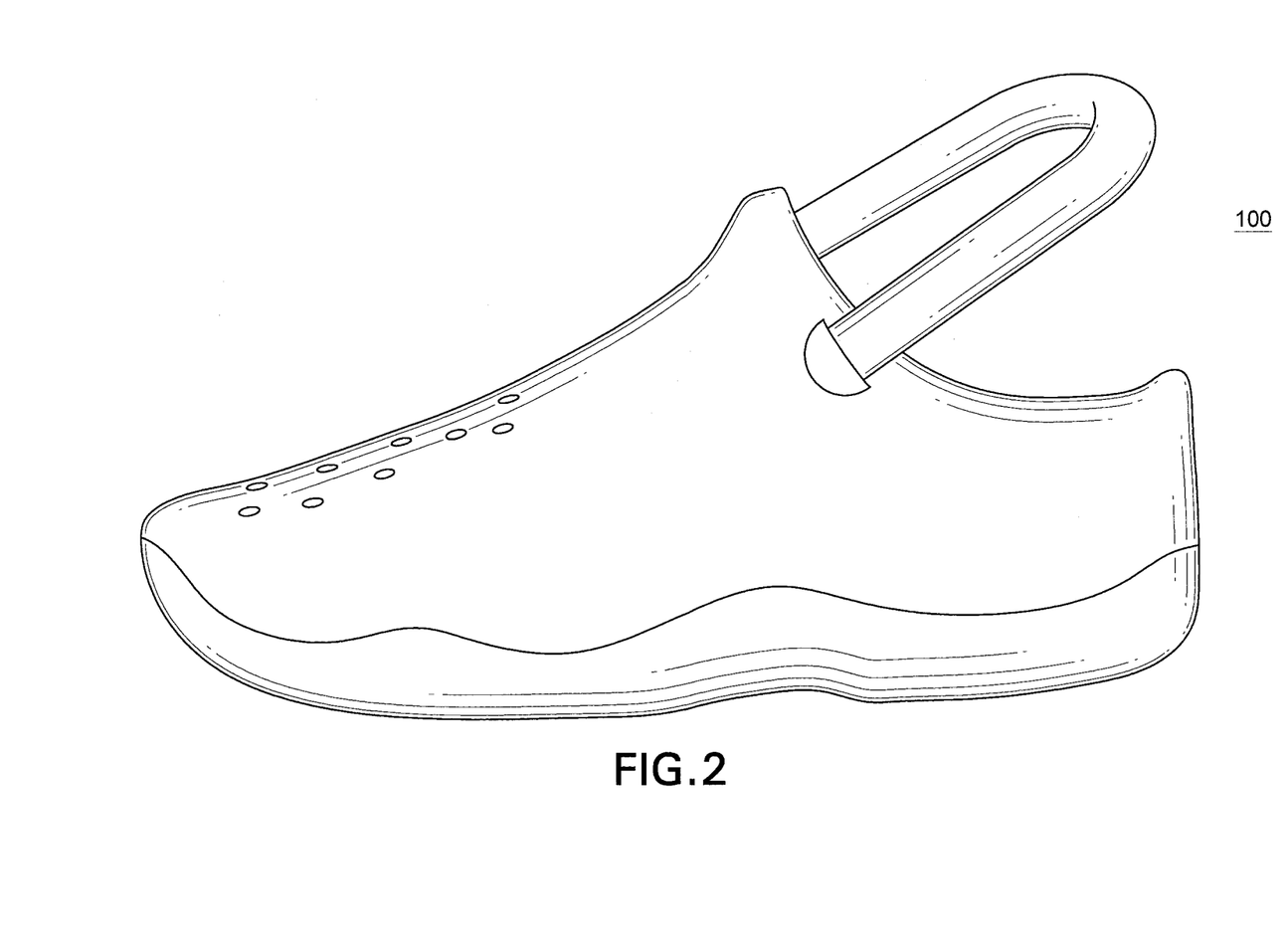
FIG. 2 is another side view of an embodiment of the present invention.

FIG. 2 is another side view of an embodiment of the present invention. It shows a solitary construction of vibrating foot massager 100. In another preferred embodiment, vibrating foot massager 100 is constructed substantially out of rubber.

Figure 3:
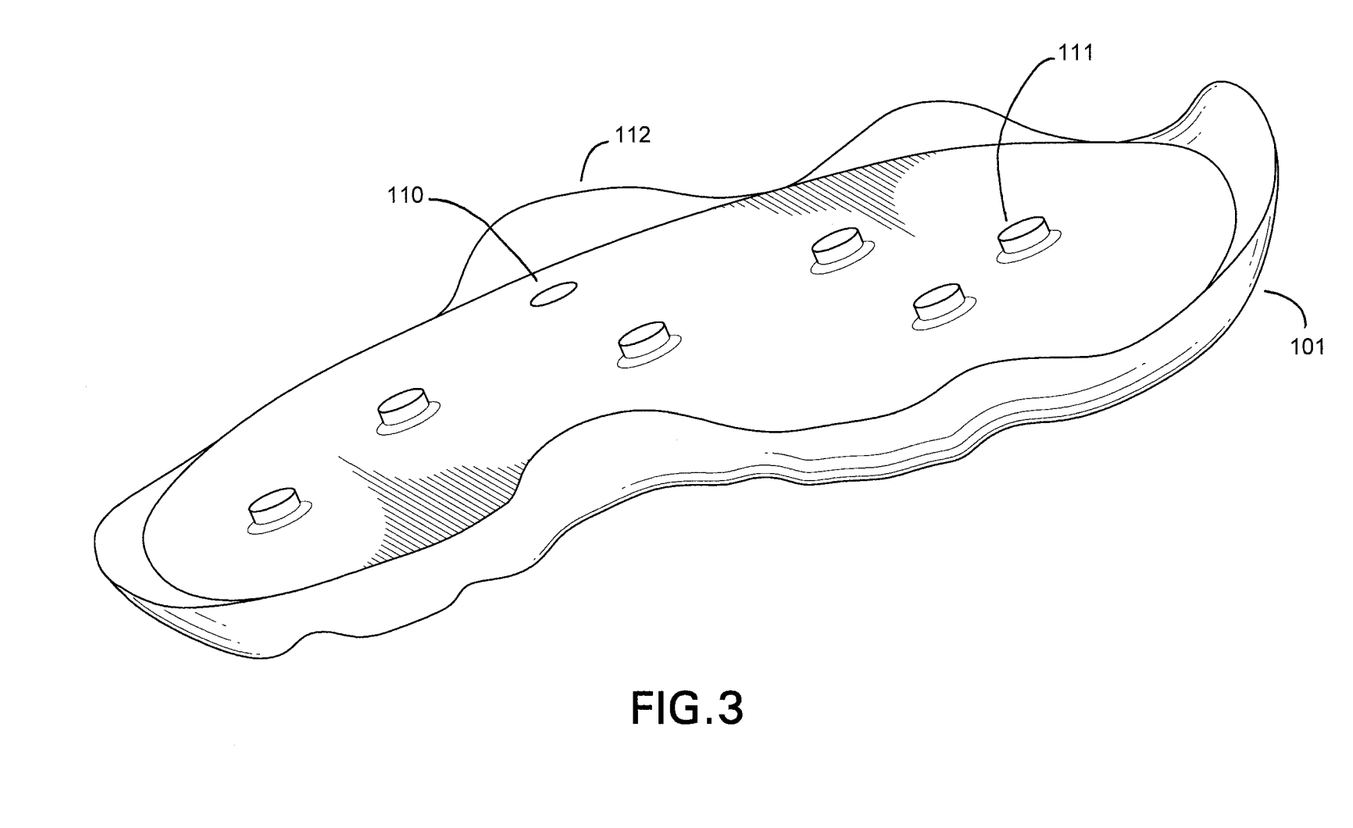
FIG. 3 is a perspective view of an embodiment of bottom portion equipped with a complete custom sole of the present invention.

Turning to FIG. 3, a perspective view of an embodiment of bottom portion equipped with a complete custom sole of the present invention is provided for. Here, bottom portion 101, raised skirt 112, terminal slot 110, and plurality of raised bumps 111 are shown. Preferably, bottom portion 101 is constructed substantially out of rubber. In another preferred embodiment, bottom portion 101 is constructed out of a rubber foam. Plurality of raised bumps 111 are used to house plurality of motors 116 (See FIG. 8). While plurality of raised bumps 111 are shown in a particular configuration here, their configuration will vary based on the location of the plurality of motors 116 (See FIG. 8), and based on which zones a user is attempting to stimulate. Terminal slot 110 is used to receive at least one terminal 113 (See FIG. 4). Raised skirt 112 serves an important purpose. In one embodiment, the present invention creates a crease between top portion 105 (See FIG. 1) and bottom portion 101. This crease allows dirt and other materials to pass through the present invention, which is why in a preferred embodiment the present invention is equipped with raised skirt 112. There, raised skirt 112 prevents any materials passing through any gap that might form between bottom portion 101 and top portion 105 (See FIG. 1).

In a preferred embodiment, the complete custom sole and bottom portion 101 will be sold as a single unit. This packaging would allow a user to purchase a number of different bottom portion 101/complete custom sole combinations depending on what area of the body a user would like to stimulate.

Figure 4:
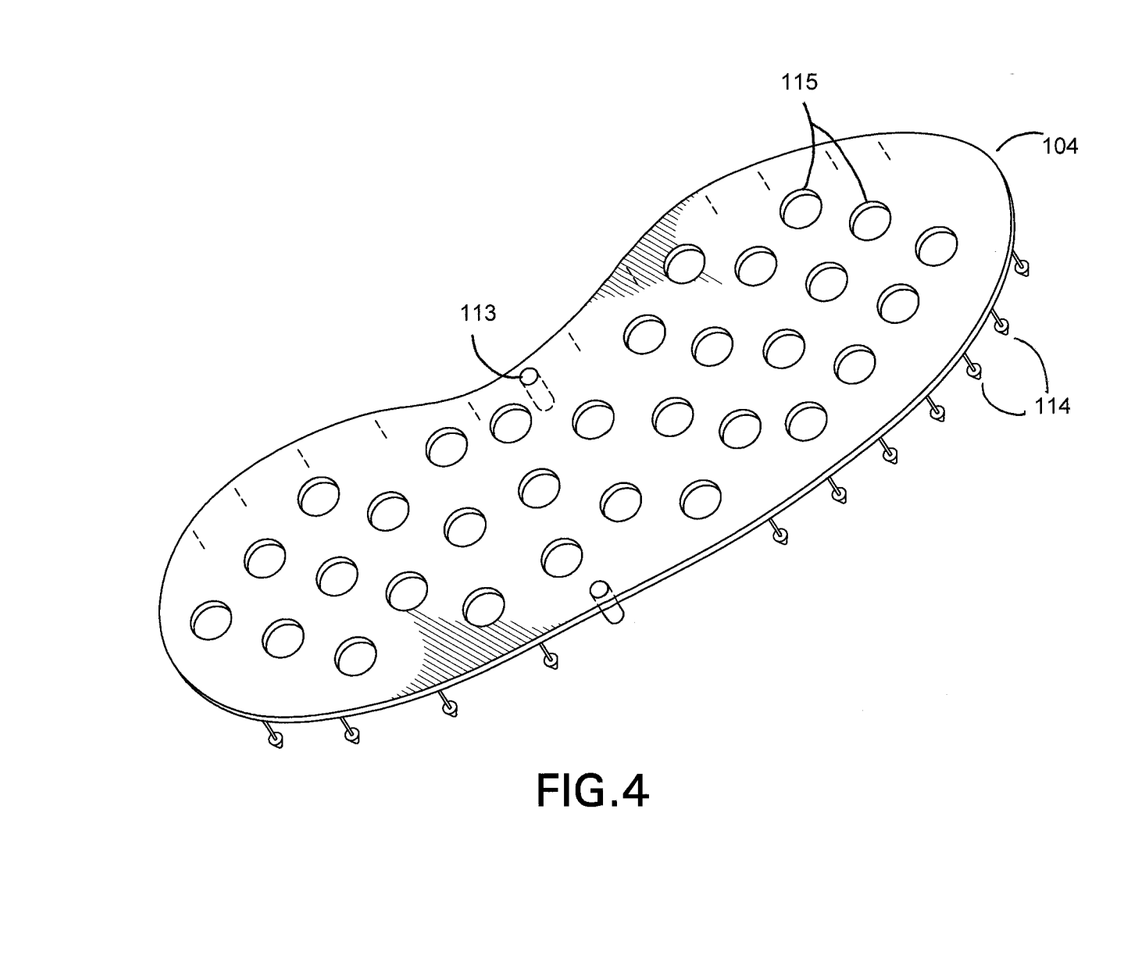
FIG. 4 is a perspective view of the interfacing sole of the present invention.

Referring to FIG. 4, is a perspective view of the interfacing sole of the present invention is provided for. This figure shows interfacing sole 104, plurality of motor slots 115, at least one terminal 113, and plurality of pegs 114. Interfacing sole attaches to the bottom-most part of top portion 105 (See FIG. 1). It is equipped with plurality of motor slots 115 to accommodate all of the different configurations that top and bottom portion of custom sole 102 and 103 may take. Accordingly, while it is possible that each of plurality of motor slots 115 will be used, there exist many embodiments where only a small fraction of plurality of motor slots 115 will be utilized at a time. At least one terminal 113 will be used as a conduit from the power source of the present invention, wherein said conduit is mediated by power switch 108 (See FIG. 1). Plurality of pegs are used to secure top portion 105 to bottom portion 101 (See FIG. 1). Preferably, these pegs are lock-in pegs, which will provide sufficient grip to allow a user to walk around wearing the present invention without worrying about top portion 105 and bottom portion 101 coming apart. In a preferred embodiment, interfacing sole and top portion 105 (See FIG. 1) are permanently affixed to each other. In another embodiment, plurality of pegs will be replaced by a plurality of magnets, such that the top and bottom portion may be removably detached with ease.

Figure 5:
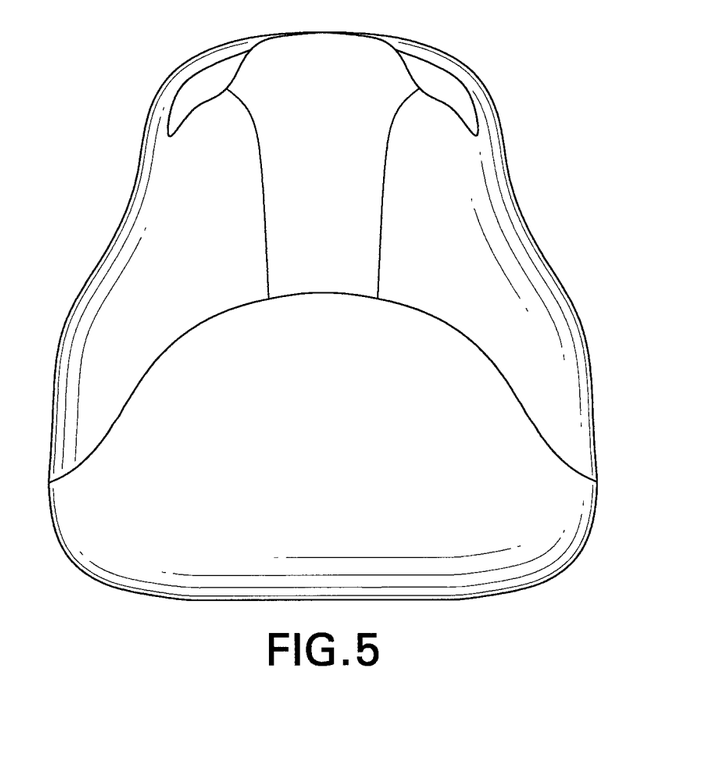
FIG. 5 is a rear view of an embodiment of the present invention.
Figure 6:
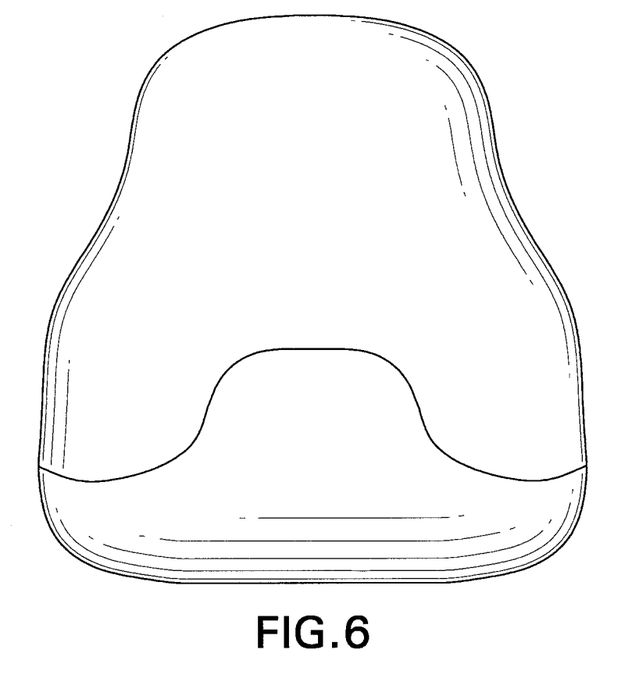
FIG. 6 is a front view of an embodiment of the present invention.

FIG. 5 is a rear view of an embodiment of the present invention and FIG. 6 is a front view of an embodiment of the present invention.

Figure 7:
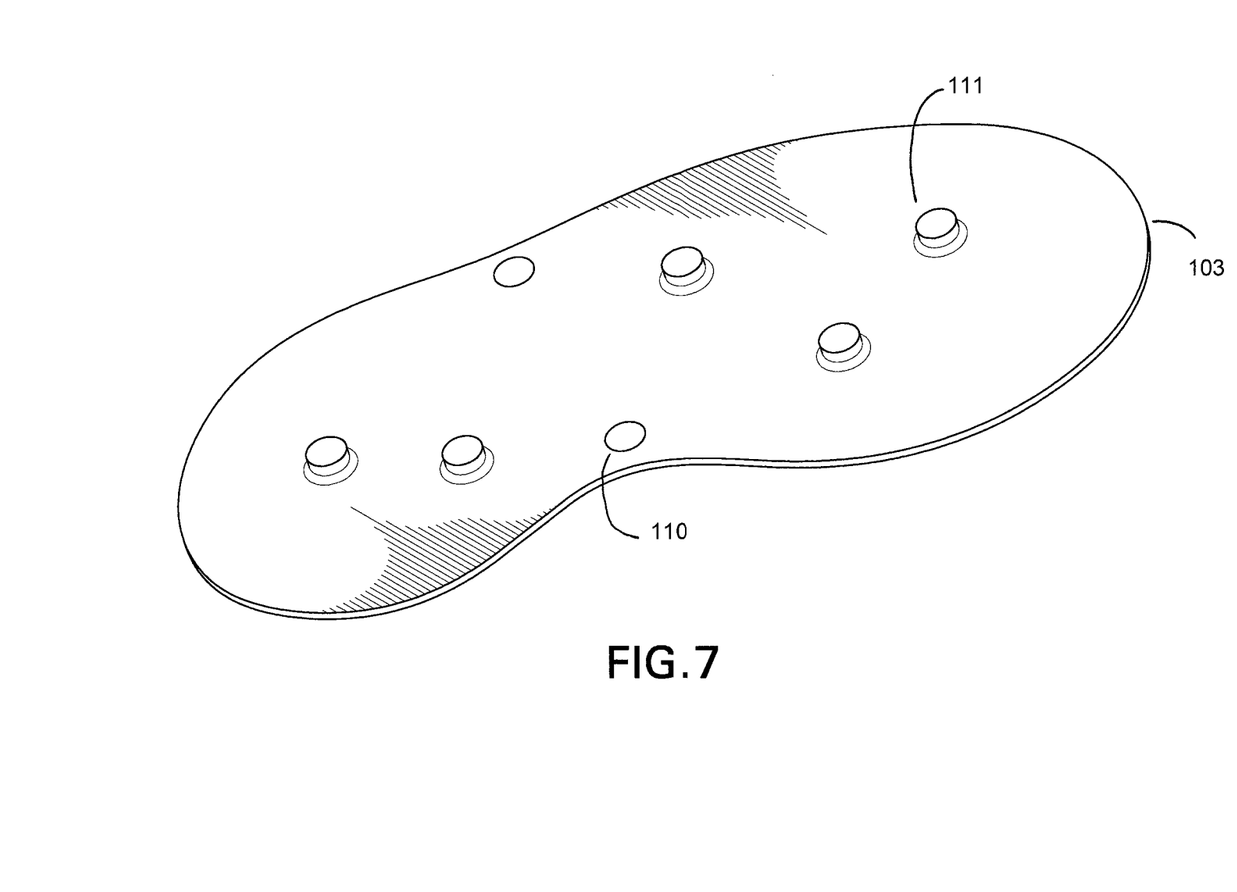
FIG. 7 is a perspective view of the top of the custom sole of the present invention.

In FIG. 7, a perspective view of the top of the custom sole of the present invention is shown. This view shows at least one terminal slot 110, plurality of raised bumps 111, and top custom sole 103. As mentioned before, at least one terminal slot 110 is used to receive at least one terminal 113, and plurality of raised bumps correspond to whatever plurality of motors 116 (See FIG. 8) have been chosen by the user.

Figure 8:
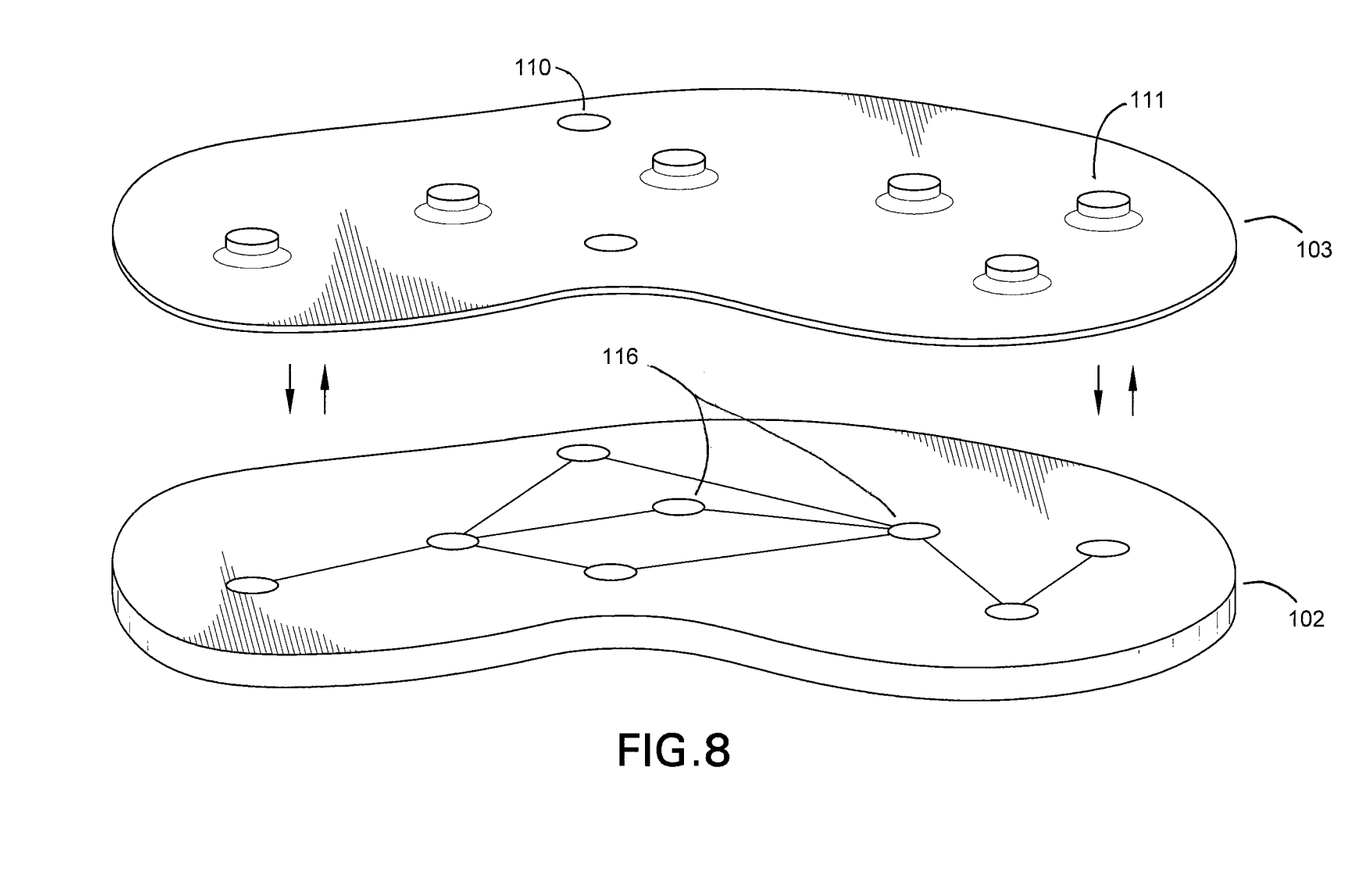
FIG. 8 is a perspective view of the top and bottom of the custom sole of the present invention.

Referring to FIG. 8, a perspective view of the top and bottom of the custom sole of the present invention is presented. Shown here are bottom custom sole 102, top custom sole 103, at least one terminal slot 110, plurality of raised bumps 111, and plurality of motors 116. As can be seen, top of custom sole 103 and bottom of custom sole 102 are shaped complimentarily. This allows for them to be properly aligned not only with each other, but with the rest of the present invention. The relative position of plurality of raised bumps 111 and plurality of motors 116 should be noted. This is because in a preferred embodiments, plurality of raised bumps 111 house plurality of motors 116.

Figure 9:
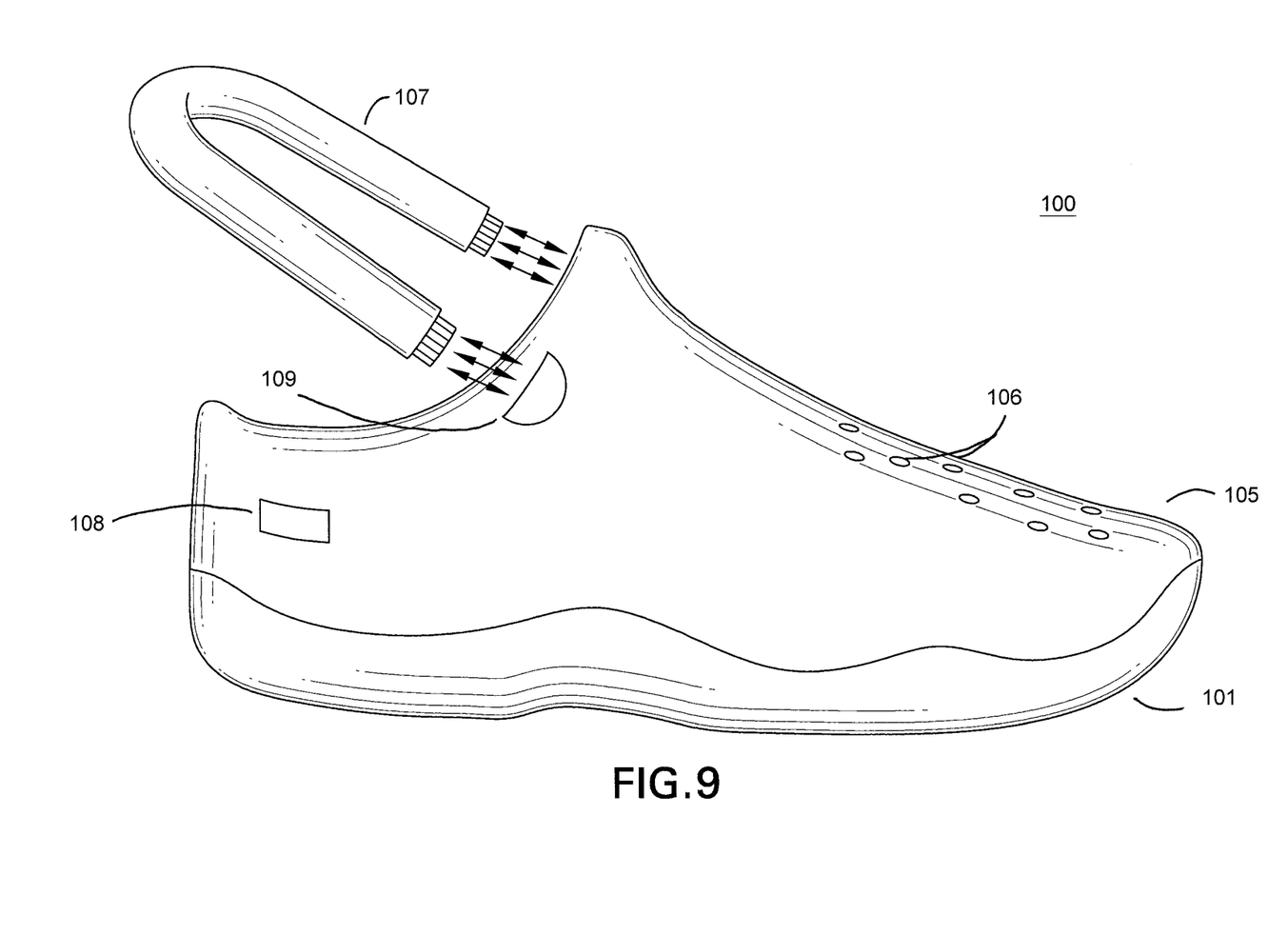
FIG. 9 is a side view of an embodiment of the present invention, highlighting the detachable nature of the strap.

In FIG. 9 a side view of an embodiment of the present invention, highlighting the detachable nature of the strap is shown. This view shows vibrating foot massager 100, plurality of holes 106, top portion 105, bottom portion 101, strap 107, connection mechanism 109, and power switch 108. This view shows a preferred embodiment, wherein strap 107 is detachable. This is beneficial because in another preferred embodiment, the power source of the present device is contained in strap 107. By strap 107 being detachable, a multitude of recharging options now exist. For example, strap 107 could be charged via an inductive mat or via solar energy. Further, the present invention could be comprised of multiple straps, allowing a user to have one strap charging while the other is in use. Connection mechanism 109 is in electronic communication with at least one terminal 113 (See FIG. 10), allowing the power source contained in strap 107 to be in electronic communication with plurality of motors 116. In yet another preferred embodiment, strap 107 is capable of utilizing self-contained batteries to power the present invention. Preferably, these will be AA batteries, although the strap can be shaped to accommodate batteries of other sizes.

In various embodiments, strap 107 can have a number of different lengths to accommodate users of various sizes, and to provide for a variety of battery capacities. Further, in a preferred embodiment, strap 107 is adjustable such that it may adjust to the size of a wide variety of users.

Figure 10:
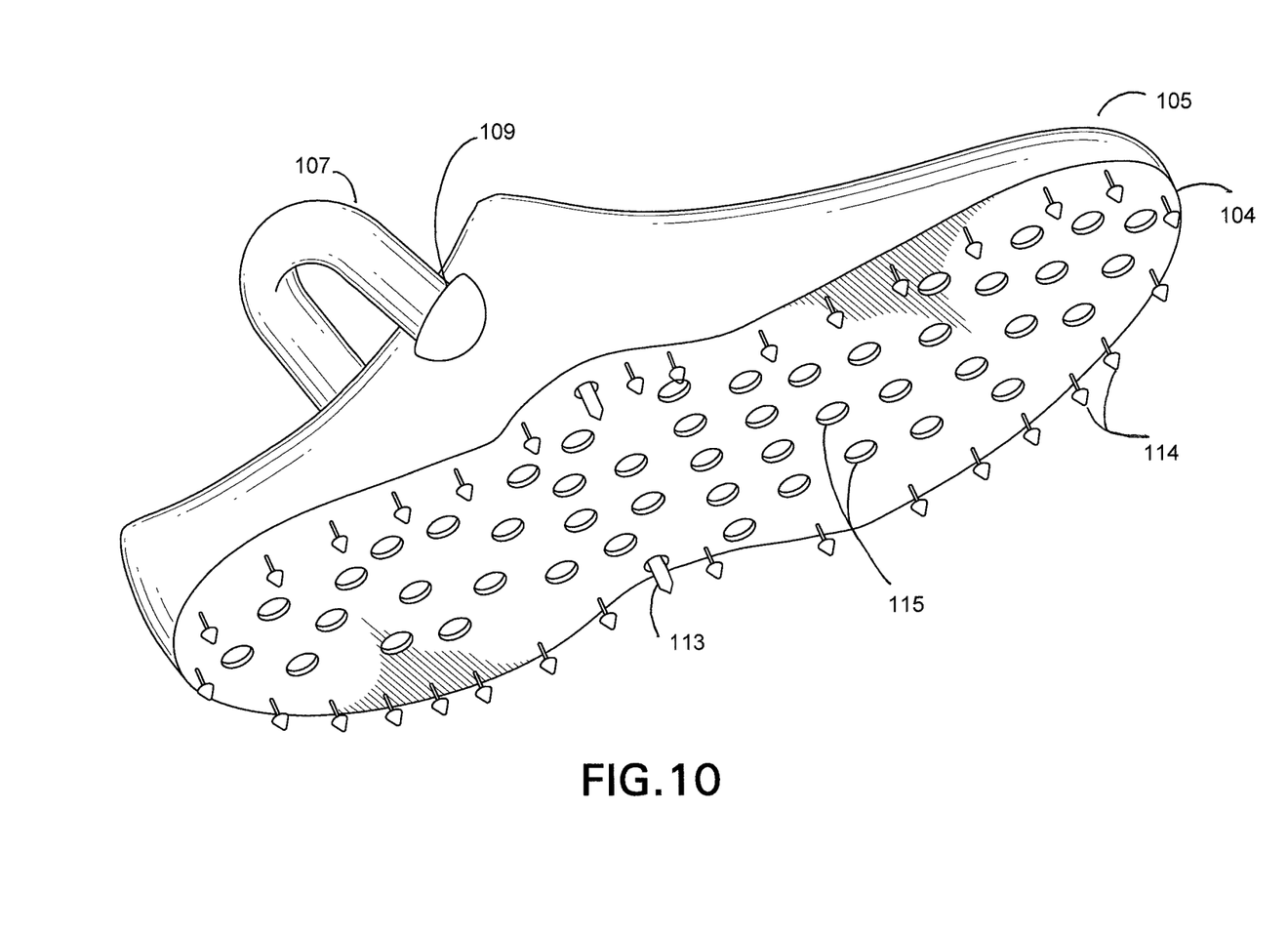
FIG. 10 is a bottom perspective view of the top portion and interfacing sole of the present invention.

Referring to FIG. 10, a bottom perspective view of the top portion and interfacing sole of the present invention is provided for. Of note here is the interaction between interfacing sole 104 and top portion 105. Also shown are plurality of motor slots 115, at least one terminal 113, and plurality of pegs 114. Here, at least one terminal 113 is shown protruding through interfacing sole 104.

In one embodiment of the present invention, the plurality of vibrating motors are controlled via a software application. In a preferred embodiment, this software application will be able to indicate to a user what areas are being massaged and which pressure points are being engaged. Further, this software will be able to track a user's use of the present invention and remind them to stimulate areas that they have been neglecting. This software application may also toggle the power and heat (if equipped) in the sandal of the present invention.

In a preferred embodiment, the body weight of a user will not stop the plurality of motors from vibrating because they are encased in bottom of custom sole 102. In some embodiments, The body weight of a user will not stop the plurality of motors from vibrating due to the motors being encased in a metal cap, or a shell as well as the fact that the plurality of raised bumps provides additional protection. In another preferred embodiment, the plurality of motors will be connected to each other via electrical wiring. Alternatively, the plurality of motors could be connected via a printed circuit board.

In an exemplary embodiment, the plurality of vibrating motors are recharged by the motion of the user walking around in the present invention. For example, the mechanism employed could be similar to that of an automatic watch.

In yet another embodiment, the top portion of the present invention can be comprised of fabric. In another embodiment of the present invention, the present inventions equipped with a wireless transceiver, allowing it to be in electronic communication with other internet-enabled electronic devices. It another embodiment, the present invention employs shockwaves to induce the electronic stimulation of a given muscle within a user. In this embodiment the frequency and strength of the stimulation can be controlled by the user. In yet another embodiment, the strap of the present invention is adorned with a plurality of LED's, preferably to be used in conjunction with product branding.

In alternative embodiments, the technology employed in the shoe of the present invention can be incorporated into pants, shirts, socks, and gloves. For example, the pants may be sport pants with micromotor gel cups or patches that can be removed and placed into many different areas on the outside of the pants. These micromotors are incorporated into gel cups which will generate heat. In one embodiment, these gel-like patches are held together by lightweight magnets. Potentially, the battery may be placed on the bottom of each leg and rest around the ankle. The pants will be insulated with a material that does not stick to a user's skin. In a preferred embodiment, the gloves will operate in a manner similar to that of the aforementioned pants with the exception that the battery will be placed around a user's wrist.

The socks of the present invention will massage your foot with a combination of micromotors and micro beads and the sock will be constructed out of a stretchy rubber or neoprene. With micro bead patches that are placed in specific areas of the sock a user may have the comfort of soft micro beads and the vibrations of the micro motors hitting your foot. The battery is placed on the top of the sock wrapping around where the ankle would be. In some embodiments, the micromotors of the present invention are removable.

The present disclosure also contemplates a neoprene sport shirt that massages the torso of your body including your arms and back, using micro motors that are in cased in gel beads that are in a form of cups or patches specifically placed to hit many areas. In one embodiment, one battery will be located around each of a user's wrist and will each be equipped with a power button. There can be a model where these gel patches can be removed and placed where you desire.

In an alternative embodiment, the plurality of motors may move freely throughout the custom sole of the present invention. In yet another embodiment, the custom sole of the present invention It should be contemplated that while the present invention is optimized for the human foot, versions for chairs, sofas, and other objects are within the scope of the present disclosure.

In one embodiment, the plurality of motors are omitted from the present invention and the plurality of raised bumps in conjunction with a user's body weight are used to stimulate a particular zone of the foot. In another embodiment, the present invention will further comprise microbeads in either the bottom portion or the custom sole.

In yet another embodiment, the present invention will be capable of warming a user's foot.

In the various embodiments, the present invention, in part or in whole, can be constructed out of a material selected from the group consisting of rubber, foam, plastic, croslite, polyurethane, polyurethane foam, vinyl and neoprene.

When introducing elements of the present disclosure or the embodiment(s) thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements.

While the disclosure refers to exemplary embodiments, it will be understood by those skilled in the art that various changes may be made and equivalents may be substituted for elements thereof without departing from the scope of the disclosure. In addition, many modifications will be appreciated by those skilled in the art to adapt a particular instrument, situation or material to the teachings of the disclosure without departing from the spirit thereof. Therefore, it is intended that the disclosure not be limited to the particular embodiments disclosed.

What is claimed is:

1. A vibrating foot massager, comprising:
   a bottom portion;
   a custom sole, having a top layer and a bottom layer,
      wherein said top layer is equipped with at least one terminal slot and a plurality of raised bumps,
      wherein said bottom layer is equipped with a plurality of motors,
      wherein said custom sole is shaped complimentarily to said bottom portion;
   an interfacing sole, equipped with a plurality of holes, a plurality of pegs, and at least one terminal
      wherein said interfacing sole is shaped complimentarily to said bottom portion and said custom sole,
      wherein said at least one terminal is inserted through said at least one terminal slot and into said bottom layer of said custom sole, and
      wherein said plurality of pegs are capable of securing said interfacing layer to said bottom portion;
   a top portion, having a power switch, a connection mechanism, and a strap connected to said connection mechanism,
      wherein said connection mechanism is connected to said at least one terminal,
      wherein said strap houses a power supply,
      wherein said power supply is operatively connected to said plurality of motors via said connection mechanism and said at least one terminal,
      wherein said power switch controls the flow of power from said power source to said at least one motor.

2. The vibrating foot massager of claim 1, wherein said bottom portion is equipped with a raised skirt.

3. The vibrating foot massager of claim 1, wherein said plurality of motors are micro coin cell motors.

4. The vibrating foot massager of claim 1, wherein said device is comprised substantially out of a material selected from the group consisting of: rubber, foam, plastic, croslite, polyurethane, polyurethane foam, vinyl and neoprene.

5. The vibrating foot massager of claim 1, wherein said top portion is capable of removably detaching from said bottom portion.

6. The vibrating foot massager of claim 5, wherein said top portion and said bottom portion employ magnets to provide for said detaching.

7. The vibrating foot massager of claim 1, wherein said bottom component is equipped with a sole.

8. The vibrating foot massager of claim 1, wherein said bottom portion is constructed substantially out of a rubber foam.

9. The vibrating foot massager of claim 1, wherein said strap is removably detachable from said connection mechanism.

10. The vibrating foot massager of claim 1, wherein said power source is at least one AA battery.

11. The vibrating foot massager of claim 1, wherein said power source is a rechargeable battery.

12. The vibrating foot massager of claim 10, wherein said power source is a removably battery is capable of being charged wirelessly.

13. The vibrating foot massager of claim 1, further comprising a plurality of holes located on said top portion.

14. The vibrating foot massager of claim 1, wherein said top portion and said bottom portion are permanently affixed.

15. The vibrating foot massager of claim 1, further comprising a gel insert.

16. The vibrating foot massager of claim 1, wherein said plurality of motors are omitted.

17. The vibrating foot massager of claim 1, wherein said bottom portion and said custom sole are permanently affixed to each other.

18. The vibrating foot massager of claim 1, wherein said top portion and said interfacing sole are permanently affixed.

19. The vibrating foot massager of claim 1, wherein said strap is adjustable in size.

* * * * *